United States Patent
Baier et al.

(10) Patent No.: US 8,435,572 B2
(45) Date of Patent: May 7, 2013

(54) COMPOSITIONS AND METHODS FOR PROMOTING A RELAXATION STATE

(75) Inventors: Christine Marie Baier, Massapequa Park, NY (US); Stephen Laczynski, Pearl River, NY (US)

(73) Assignee: ELC Management, LLC, New York, NY (US)

(*) Notice: Subject to any disclaimer, the term of this patent is extended or adjusted under 35 U.S.C. 154(b) by 0 days.

(21) Appl. No.: 13/129,720

(22) PCT Filed: Oct. 12, 2009

(86) PCT No.: PCT/US2009/060320
§ 371 (c)(1),
(2), (4) Date: Nov. 1, 2011

(87) PCT Pub. No.: WO2010/065194
PCT Pub. Date: Jun. 10, 2010

(65) Prior Publication Data
US 2012/0040028 A1      Feb. 16, 2012

Related U.S. Application Data

(60) Provisional application No. 61/119,564, filed on Dec. 3, 2008.

(51) Int. Cl.
*A61K 36/00* (2006.01)
*A61K 36/53* (2006.01)
*A61K 36/28* (2006.01)
*A61K 36/736* (2006.01)

(52) U.S. Cl.
USPC ................ 424/725; 424/764; 424/735

(58) Field of Classification Search .................... None
See application file for complete search history.

(56) References Cited

U.S. PATENT DOCUMENTS

| | | |
|---|---|---|
| 4,670,463 A | 6/1987 | Warren et al. |
| 4,671,959 A | 6/1987 | Warren et al. |
| 5,141,921 A | 8/1992 | Sawano et al. |
| 6,268,333 B1 | 7/2001 | Okazaki et al. |
| 6,830,755 B2 * | 12/2004 | Librizzi et al. ............... 424/401 |
| 7,169,746 B2 | 1/2007 | Shoji et al. |
| 2004/0241186 A1 | 12/2004 | Huang |
| 2004/0242452 A1 | 12/2004 | Shoji et al. |
| 2005/0207982 A1 | 9/2005 | Jendrucko et al. |
| 2005/0287232 A1 | 12/2005 | Hosoi et al. |
| 2008/0044499 A1 | 2/2008 | Ozeki et al. |

FOREIGN PATENT DOCUMENTS

| | | | |
|---|---|---|---|
| JP | 2000-355545 A | | 12/2000 |
| JP | 2000355545 A | * | 12/2000 |
| KR | 2004-0055713 A | | 6/2004 |
| RU | 2262919 C1 | * | 10/2005 |
| WO | WO 2005/062730 A2 | * | 7/2005 |

OTHER PUBLICATIONS

Mintel GNPD; http://www.gnpd.com; Mega-Mushroom Eye Serum; Record ID: 653604; Origins Natural Resources; Dr. Andrew Weil for Origins Plantidote; Skincare; Eye Care; France; Jan. 2007.
Nagai, et al.; NeuroImage; Brain activity relating to the contingent negative variation: an fMRI investigation: NeuroImage; vol. 21; pp. 1232-1241; 2004.
The Psychophysiological Effects of Odors, Aromachology; Review of the latest researches on the effects of odors; Takasago International Corporation; Tokyo, Japan; pp. 1-16; Nov. 1991.
PCT International Search Report; International Application No. PCT/US2009/060320; Completion Date: Jun. 24, 2010; Mailing Date: Jun. 24, 2010.
PCT Written Opinion of the International Searching Authority; or the Declaration; International Application No. PCT/US2009/060320; Completion Date: Jun. 24, 2010; Mailing Date: Jun. 24, 2010.
Burns, E., Blarney C., "Using aromatherapy in childbirth," Nursing Times, 90(9), pp. 54-60, 1994.
Hongratanaworakit, T., "Physiological effects in aromatherapy," Songklanakarin J. Sci, Technol., 26(1), pp. 117-125, 2004.

* cited by examiner

*Primary Examiner* — Qiuwen Mi
(74) *Attorney, Agent, or Firm* — Julie M. Blackburn

(57) ABSTRACT

A topical composition for inducing relaxation upon application to skin comprising a mixture of mandarin oil, lavender oil, chamomile oil, and optionally sweet almond oil; and a method for inducing sleep and/or a relaxation state by topically applying the composition.

10 Claims, 2 Drawing Sheets

COMPOSITIONS AND METHODS FOR PROMOTING A RELAXATION STATE

This application is a national stage filing of PCT/US2009/060320, filed Oct. 12, 2009, and claims priority from U.S. 61/119,564, filed Dec. 3, 2008.

TECHNICAL FIELD

The invention is in the field of methods and compositions for topical application to induce sleep or a relaxation state.

BACKGROUND OF THE INVENTION

Agitation, stress, and insomnia plague many people particularly with the pressures of modern life. There are a wide variety of ingestibles that promote relaxation or sleep inducement. Chamomile tea is well known to promote relaxation and induce sleep. There are also herbs and vitamins that are effective for this purpose. For example, melatonin, Passion Flower, Valerian extract, and St. John's Wort are well known for their ability to induce a relaxation state. Other options include prescription pharmaceuticals, many of which can be addictive and have other harmful effects.

The current trend is "natural" and 'organic". People want to use products that are not only safe for them but environmentally friendly in that the products are biodegradable, contain raw materials that are green, or are sold in packaging that is not synthetic. This is particularly desirable when it comes to products that may be used to induce relaxation. It is most desirable to have products that can be applied topically and sensory qualities that provide a relaxation state.

Unexpectedly, it has been discovered that a certain blend of plant oils is excellent for inducing a state of relaxation and sleep, causing a reduction in stress level, encouraging relaxation, improving the quality of sleep and promoting the general ability to unwind or soothe yourself so that sleep and/or relaxation states can be attained more easily.

It is an object of the invention to provide a composition for topical application that induces relaxation and reduces stress levels.

It is another object of the invention to provide a composition for topical application that promotes sleep.

It is another object of the invention to provide a method for inducing relaxation or sleep by topically applying a composition containing a certain blend of plant oils.

SUMMARY OF THE INVENTION

The invention is directed to a topical composition for inducing relaxation upon application to skin comprising a plurality of plant extracts which, together, have a Contingent Negative Variation (CNV) value ranging from about −1 to about −100.

The invention is also directed to a topical composition for inducing relaxation upon application to skin comprising a mixture of mandarin oil, lavender oil, chamomile oil, and optionally sweet almond oil.

The invention is further directed to an environmentally scented product for inducing relaxation comprising a mixture of mandarin oil, lavender oil, chamomile oil, and, optionally, sweet almond oil.

The invention is further directed to a method for inducing sleep by topically applying a composition comprising a mixture of mandarin oil, lavender oil, chamomile oil, and optionally sweet almond oil.

The invention is further directed to a method for inducing relaxation by topically applying a composition comprising a mixture of mandarin oil, lavender oil, chamomile oil, and optionally sweet almond oil.

The invention is further directed to a method for inducing relaxation by providing an environmentally scented product comprising a mixture of mandarin oil, lavender oil, chamomile oil, and optionally sweet almond oil.

DETAILED DESCRIPTION

I. The Mixture

Figure 1:
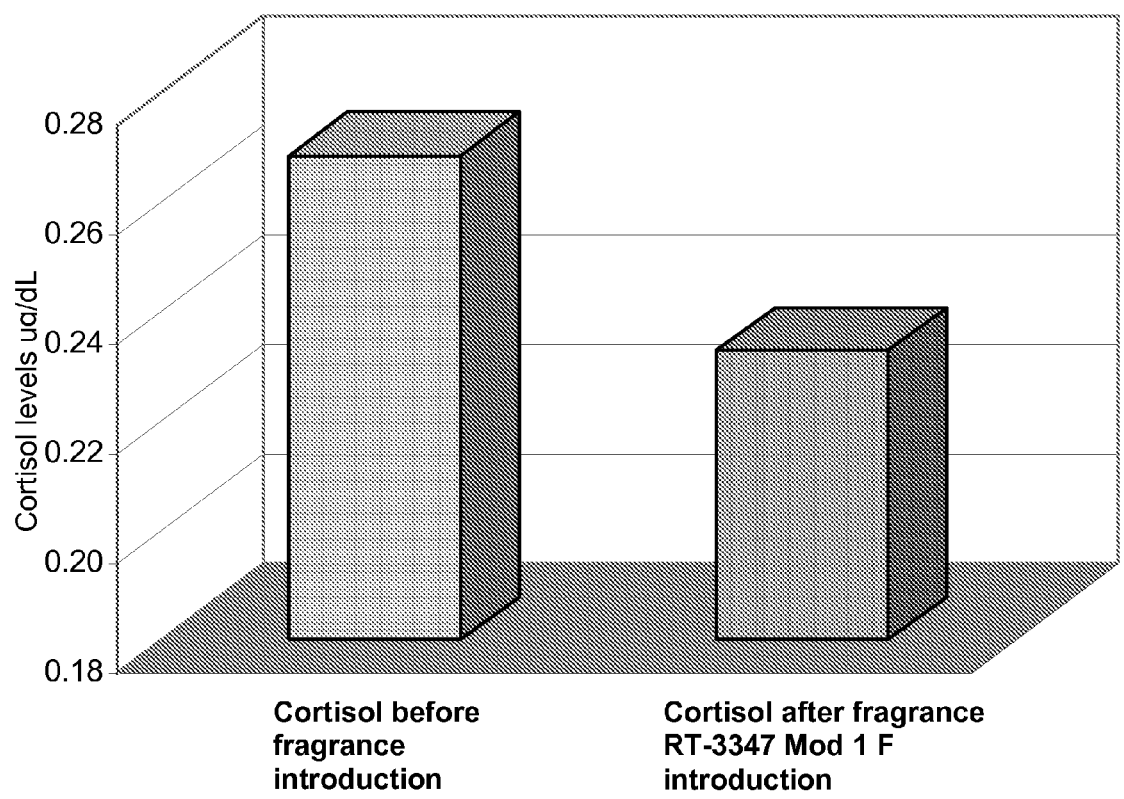
FIG. 1 depicts the before and after test results of saliva samples collected from panelists before and after exposure to the Mixture (as defined below).

The relaxation and sleep inducing properties of the topical compositions of the invention are due to a mixture of certain plant materials that, when combined, provide a CNV of −1 to about −100 when tested according to standard CNV test protocol (as referenced in The Psychophysiological Effects of Odors, Aromachology—Review of the Latest Researches on the Effects of Odors, Takasago International, November 1991). Specifically, CNV is measured by attaching electrodes to the scalp to monitor shifts in brain waves both before and after the test subject has sniffed a particular fragrance. The test is performed repeatedly, e.g. 10-20 trials, after which the results are averaged. The ability of a fragrance to cause a decrease in CNV (that is less a CNV value less than zero) means that the fragrance is a sedative. When the CNV is increased, that is, has a value greater than zero, the fragrance is a stimulant. While a specific ingredient may itself provide a positive CNV, when it is combined with other ingredients that may either have a positive or negative CNV, the mixture could have a negative CNV. This is why the CNV measurement must be determined by testing the mixture or the individual ingredient that is to be incorporated into the composition. One cannot assume that a combination of ingredients with a negative CNV value will each individually have a negative CNV.

In one preferred embodiment, a suitable composition comprises mandarin oil, lavender oil, chamomile oil, and optionally sweet almond oil (the "Mixture"). Preferably the oils range from about 1-45% mandarin oil, 1-45% lavender oil, 1-45% chamomile oil, and, if present 1-45% sweet almond oil. The oils are obtained by extraction from mandarin orange, lavender, chamomile, and almonds. One of the Mixtures may be purchased from Takasago Corporation, Rockleigh, N.J., under the trade name "RT-3347 Mod 1F" which is a mixture of mandarin oil, lavender oil, chamomile oil, and sweet almond oil. Another Mixture may be purchased from Takasago Corporation under the tradename "RU-1766" which is a mixture of mandarin oil, lavender oil, and chamomile oil. Preferably from about 0.01 to 60%, more preferably from about 0.05 to 30%, most preferably from about 0.1 to 25% of the Mixture is used in the compositions of the invention. All percentages mentioned herein are percentages by weight unless otherwise indicated.

II. The Composition

The mixture of oils is incorporated into compositions that may be applied topically to the body, face, lips, nails or hair. The composition may be in the anhydrous form or in the aqueous gel or emulsion form. If in the aqueous gel form, the composition comprises from about 0.1 to 99.5% water. If in the emulsion form, the composition may be a water in oil or oil in water emulsion comprising from about 0.5 to 95%, preferably, 1 to 85%, more preferably from about 5 to 80% water; and from about 0.5 to 95%, preferably from about 1 to 85%, more preferably from about 5 to 80% oil.

A. Oils

Suitable oils may include silicone oils, natural plant oils, organic oils, hydrocarbon oils, and the like. The term "oil" means an ingredient that is preferably pourable at room temperature (e.g. 25° C.).

1. Silicone Oils

Suitable silicone oils include volatile or non-volatile silicones. The term "volatile" means that the silicone has a vapor pressure of greater than about 2 mm of mercury at 20° C. The term "nonvolatile" means that the silicone has a vapor pressure of less than about 2 mm. of mercury at 20° C. Suitable volatile silicones may be linear or cyclic. Examples of linear volatile silicones include hexamethyldisiloxane (0.5 centstokes), octamethyltrisiloxane (1.0 centistokes), decamethyltetrasiloxane (1.5 centistokes), and dodecamethylpentasiloxane (2.0 centistokes). Examples of cyclic volatile silicones include octamethylcyclotetrasiloxane, decamethyltetracyclosiloxane, dodecamethylpentasiloxane, and the like. Examples of nonvolatile silicones include dimethicone, phenyl dimethicone, phenyl trimethicone, trimethylsiloxyphenyldimethicone, cetyl dimethicone, and the like. If present the silicone oils may range from about 0.1 to 85%.

2. Natural Plant Oils

Also suitable as the oil component are one or more natural plant oils including oils from the fruits, seeds, roots, or other parties of plants such as sunflower, safflower, jojoba, olive, soybean, coconut, castor, canola, palm, sesame, macadamia, mango, rice, and so on. If present such oils may range from about 0.5 to 99%, preferably from about 1-95%, more preferably from about 5 to 85% of the composition.

B. Alcohols

The compositions of the invention may also contain one or more mono-, di-, or polyhydric alcohols. If present, ranges may be from about 0.1 to 99%, preferably from about 0.5 to 95%, more preferably from about 3 to 90%.

Suitable monohydric alcohols include C2-20 aliphatic or aromatic mono hydroxyl substituted alcohols such as ethanol, propanol, butanol, bisabolol, benzyl alcohol, and mixtures thereof.

Suitable dihydric alcohols include $C_{2-6}$ alkylene glycols such as ethylene glycol, propylene glycol, butylene glycol, pentylene glycol, hexylene glycol, and mixtures thereof.

Suitable polyhydric alcohols include glycerin, or sugar alcohols such as erythritol, arabitol, xylitol, ribitol, or mixtures thereof.

C. Fatty Acids

The composition may contain one or more fatty $C_{6-30}$ carboxylic acids that may be aliphatic, aromatic, saturated or unsaturated. Such fatty acids may be liquid or solid at room temperature and include stearic, isostearic, palmitic, behenic, lauric, linoleic, linolenic, myristic, oleic, ricinoleic, or mixtures thereof. If present, the fatty acid may range from about 0.1 to 40%, preferably from about 0.5 to 35%, more preferably from about 0.5 to 25% of the composition.

D. Fatty Alcohols

The composition may also contain one or more fatty C12-30 alcohols such as cetyl, behenyl, caprylic, cetearyl, stearyl, isostearyl, oleyl, linoleyl, lauryl alcohols and mixtures thereof. If present the fatty alcohol may range from about 0.1 to 65%, preferably from about 0.5 to 60%, more preferably from about 1 to 50% of the composition.

E. Structuring Agent

The composition may also contain one or more structuring agents which may act as thickeners for the aqueous phase of the composition, when such compositions are in the aqueous form. If present the structuring agent may range from about 0.1 to 35%, preferably from about 0.5 to 30%, more preferably from about 1 to 25% of the composition. Suitable structuring agents include synthetic polymers that may be homo- or copolymers of acrylic acid, methacrylic acid, or their simple C1-6 alkyl esters or acrylamides. These polymers may be crosslinked Examples of such agents include carbomer (a homopolymer of acrylic acid crosslinked with a polyfunctional agent which may be the allyl ether of sucrose, pentaerythritol, or propylene), C10-30 alkyl acrylate crosspolymer, acrylamide sodium acrylate copolymer, acrylamide sodiumacryloyldimethyltaurate copolymer, acrylates steareth-20 methacrylate copolymer, acrylamides copolymer, acrylates vinylneodecanoate crosspolymer, and so on.

Also suitable are naturally occurring or synthetic gums or hydrocolloids including but not limited to agar, algin, cellulose, xanthan gum, chitin, and mixtures thereof.

F. Esters of Polyols or Alkylene Glycols

It may also be desirable to include one or more emulsifying agents in the form of polyol esters of esters of C2-4 alkylene glycols. More preferred is a $C_{2-4}$ alkylene glycol or polyol ester of a $C_{12-30}$ fatty carboxylic acid. The alkylene glycol may preferably be ethylene or propylene glycol having from about 2 to 200 repeating units, and the fatty carboxylic acid is selected from stearic acid or isostearic acid. Most preferred are esters of polyols such as glycerin and C2-4 alkylene glycols such as ethylene glycol, and where the fatty carboxylic acid is stearic or isostearic acid. Examples of such ingredients include glyceryl stearate, diglyceryl diisostearate, PEG-2-100 stearate or isostearate, and the like. Most preferred is glyceryl stearate, PEG-100 stearate or mixtures thereof. If present such emulsifying agents may range from about 0.1 to 40%, preferably from about 0.5 to 35%, more preferably from about 0.5 to 30% of the composition.

G. Alkoxylated Alcohols

It may also be desirable to incorporate various types of alkoxylated alcohols in to the composition. If present, suggested ranges are from about 0.1 to 30%, preferably from about 0.5 to 25%, more preferably from about 1 to 20% of the composition. Suitable alkoxylated alcohols include $C_{6-30}$ aromatic or aliphatic fatty alcohols that may be unsaturated or saturated, which are reacted with alkoxy groups, preferably ethoxy or propoxy groups having from about 1 to 200 repeating ethoxy or propoxy units. Examples of fatty alcohols include cetyl, stearyl, isostearyl, behenyl, myristyl, and the like. Such alkoxylated alcohols may have from about 1 to 200 repeating ethoxy or propoxy groups. Examples include ceteareth, beheneth, steareth, isosteareth, and the like where the number of repeating ethoxy groups ranges from about 2 to 200.

H. Botanical Extracts

The composition may contain one or more botanical extracts derived from plant seeds, fruit, pulp, root, or leaves. Examples include extracts from the *Siegesbeckia Orientalis, Acmella Oleracea, Calluna, Ascophyllum, Helianthus, Triticum, Olea, Astrocaryum, Ononotus, Menyanthes, Cladosiphon, Silybum, Cocos, Carthamus*, genuses and the like. More specific examples of suitable extracts include *Siegesbeckia, Castanea Sativa, Acmella, Calluna, Ascophyllum Nodosum, Helianthus Annus, Triticum Vulgare, Olea Europa, Astrocaryum Murumuru, Ononotus Obliquus, Menyanthes Trifoliata, Cladosiphon Okamuranas, Silybum Marianum,*

*Cocos Nucifera, Carthamus Tinctorius*, and mixtures thereof. If present such botanical extracts may range from about 0.001 to 20% of the composition.

I. Vitamins or Antioxidants

The composition may also contain one or more vitamins or antioxidants. If present they may range from about 0.001 to 10% of the composition. Suitable vitamins include E, C, A, K, D, or derivatives thereof. Examples include tocopheryl acetate, tocopherol maleate, ascorbyl palmitate, magnesium ascorbyl phosphate, or mixtures thereof.

II. The Products

The compositions of the invention may be in the form of bath or body oils, facial or body creams or lotions, hand or body lotions, sprays, aromatherapy products and the like.

For example, one preferred composition is bath oil for use in pouring into bath water prior to bathing such that the oils and active ingredients present in the bath water will coat the skin and provide an aroma that will induce relaxation. The bath oil is preferably anhydrous and has from about 5 to 99% of oils, preferably naturally occurring plant oils, and from about 0.1 to 20% of the Mixture.

Another preferred composition is a facial cream to be applied to the face prior to sleep or inducement of the relaxation state. Such cream is preferably in the water and oil emulsion form comprising from about 0.5 to 95%, preferably, 1 to 85%, more preferably from about 5 to 80% water; and from about 0.5 to 95%, preferably from about 1 to 85%, more preferably from about 5 to 80% oil. The oils may be any of the oils set forth above with respect to the composition and in the percentages stated. Most preferred is a facial cream comprising:

20 to 95% water, 0.1 to 20% of a dihydric or polyhydric alcohol, 0.1 to 40% dimethicone, 0.01 to 20% carbomer, 0.1 to 10% fatty acids, from about 0.01 to 20% botanical extracts.

Another preferred composition is a body balm applied to face and skin prior to retiring or the time when it is desired to induce a relaxation state. The balm preferably is in the emulsion form and comprises from about 50-95% water, 0.5 to 15% of an ester of an alkylene glycol or polyol and a fatty carboxylic acid as described herein, from 0.1 to 10% of the Mixture, from about 0.001 to 20% dimethicone, and from about 0.01 to 10% of one or more dihydric alcohols, and from about 0.1 to 40% of an aqueous phase structuring agent that is a synthetic polymer comprised of acrylic acid, methacrylic, acid or their simple esters, or acrylamide; or one or more hydrophilic colloids such as xanthan gum.

Another type of composition may be in the form of a spray applied to the body using a spritzer device or similar. Such a spray is generally aqueous based and comprises from about 5 to 99% water, from about 5 to 80% of one or more mono-, di-, or polyhydric alcohols, and the Mixture.

The following more specific examples of suitable compositions are set forth for the purposes of illustration only.

EXAMPLE 1

| Ingredient | % by weight | | |
|---|---|---|---|
| | Night Cream | Night Balm | Bath Oil |
| Water | QS | QS | |
| *Helianthus Annus* (Sunflower) seed oil | | | QS |
| *Carthamus Tinctorius* (Safflower) seed oil | | | 15.00 |
| *Simmondsia Chinensis* (Jojoba) seed oil | | | 5.00 |
| *Olea Europa* (Olive) fruit oil | | | 2.00 |
| Tricaprylin | | 16.00 | |
| Sweet almond oil | | 4.00 | |
| Emulsifying wax NF | | 3.00 | |
| *Cocos Nucifera* (Coconut) oil | | | 2.40 |
| Caprylic/capric triglyceride | 12.00 | | |
| Caprylyl glycol/phenoxyethanol/hexylene glycol | | 0.70 | |
| Myristyl myristate | 5.00 | | |
| Dicaprylyl maleate | 2.50 | | |
| Cetearyl alcohol/ceteareth-20 | 2.00 | | |
| Stearic acid | 2.00 | | |
| Cetyl alcohol | 1.60 | 1.80 | |
| Candelilla wax | | 0.05 | |
| Behenyl alcohol | 1.60 | | |
| PEG-100 stearate/glyceryl stearate | 1.50 | 5.00 | |
| Potassium sorbate | | 0.10 | |
| Phenoxyethanol/cholorphenesin/glycerin/sorbic acid | 1.40 | | |
| Bis-diglyceryl polyacyladipate-2 | 1.30 | 0.07 | |
| Butylene glycol | 1.00 | 1.00 | |
| PEG-100 stearate | 1.00 | | |
| *Glycine Soja* (soybean) sterols | 1.00 | | |
| Yeast extract | 1.00 | | |
| Water/*Castanea Sativa* (Chestnut) seed extract | 1.00 | | |
| Polysorbate 20 | 0.75 | 0.50 | |
| Mixture of Mandarin, Lavendar, Chamomile, Sweet Almond Oil | 0.55 | 2.00 | 3.00 |
| *Butyrospermum Parkii* (Shea butter) | | 0.50 | |
| Glycerin | | 0.50 | |
| Ethylhexyl glycerin | | 0.30 | |
| Tocopheryl acetate | 0.50 | | 0.05 |
| Trehalose | 0.50 | | |
| Alcohol/water/*Acmella Oleracea* extract | 0.50 | | |
| Water/butylene glycol/*Calluna Vulgaris* (Heather) extract | 0.50 | | |
| Dimethicone | 0.90 | 0.10 | |
| Potassium hydroxide | 0.49 | | |
| Carbomer | 0.44 | 0.25 | |
| Sorbitol/water/*Ascophyllum Nodosum* extract/*Asparagopsis Armata* extract | 0.25 | | |
| Linoleic acid | 0.20 | | |
| Cholesterol | 0.20 | | |
| Water/*Helianthus Annus* (Sunflower) seed extract | 0.20 | | |
| Wheat (*Triticum Vulgare*) Bran Extract/Olive (*Olea Europa*) extract | 0.20 | | |
| Hydrolyzed corn protein/hydrolyzed wheat protein/hydrolyzed soy protein | 0.20 | | |
| *Astrocaryum Murmuru* seed butter | 0.20 | | |
| Phenoxyethanol | 0.12 | 0.40 | |
| Disodium EDTA | 0.10 | 0.10 | |
| *Siegesbeckia Orientalis* extract | 0.10 | | |
| *Ionotus Obliquus* (Mushroom) extract/cellulose | 0.10 | | |
| Water/lecithin/*Micrococcus* lysate | 0.10 | | |
| Pantethine | 0.10 | | |
| *Olea Europaea* (Olive) leaf extract | 0.10 | | |
| Adenosine phosphate | 0.06 | | |
| Magnesium ascorbyl phosphate | 0.05 | | |
| *Menyanthes Trifoliata* leaf extract | 0.05 | | |
| Sorbic acid | 0.05 | | |
| Xanthan gum | 0.04 | 0.02 | |
| Potassium hydroxide | | 0.25 | |
| Sodium hyaluronate | 0.01 | | |
| Phosphoric acid | | 0.0001 | |
| *Cladosiphon Okamuranus* extract/dextrin | 0.01 | | |
| Lady's Thistle (*Silybum Marianum*) fruit extract | 0.001 | | |

The products were made by combining the ingredients and mixing well.

EXAMPLE 2

A body spray composition was made as follows:

| Ingredient | weight % |
| --- | --- |
| Water | QS |
| SD alcohol 40B | 38.58 |
| Laureth-4 | 4.00 |
| Butylene glycol | 3.8 |
| Polysorbate 20 | 2.65 |
| Mixture of Mandarin, Lavender and Chamomile oils | 2.00 |

The composition was prepared by combining the ingredients and mixing well.

EXAMPLE 3

The components of the Mixture (mandarin oil, lavender oil, chamomile oil and sweet almond oil) were tested for ability to reduce salivary cortisol concentration. It is known that reduced cortisol levels are associated with improved sleep. Salivary cortisol concentration is indicative of blood cortisol concentration with a reduced cortisol concentration being associated with improved relaxation.

Figure 2:
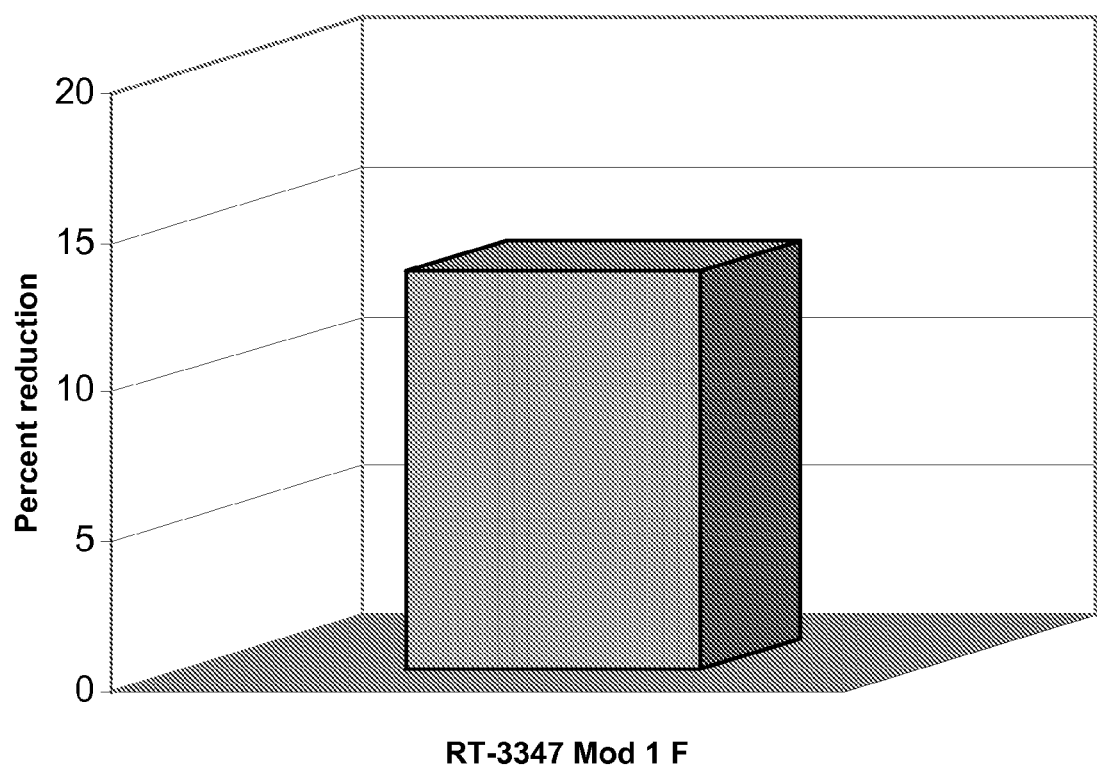
FIG. 2 depicts the reduction in cortisol in saliva samples as a result of exposure to the Mixture.

The Mixture was tested on five panelists who were advised not to consume milk products at least one hour prior to the testing. Saliva samples were collected at 9 a.m. The Mixture (referred to as RT-3348 Mod 1F) was applied above the lip using a cotton applicator. After 15 minutes a second saliva sample was collected. The saliva samples were frozen at −80° C. Prior to performing the analysis, the frozen samples were thawed and centrifuged at 3000 rpm for 30 minutes. An enzyme immunoassay purchased from Salimetrics (Cortisol Salivary Assay Kit, salimetrics.com) was used to assay the saliva supernatant for the presence of cortisol according to the kit directions. The percentage difference in cortisol level between the pre- and post-exposure to the Mixture was calculated. The results of pre- and post-fragrance exposure are set forth in FIG. 1. The percentage reduction in salivary cortisol as a result of exposure to the Mixture (RT-3348 Mod 1F) is as set forth in FIG. 2.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A method for inducing sleep by topically applying a skin care composition comprising a from 0.01 to 60% by weight of the total composition of a Mixture containing 1-45% mandarin oil, 1-45% lavender oil, 1-45% chamomile oil, and 1-45% sweet almond oil, with all percentages in the Mixture by weight of the total Mixture, to the skin in an amount sufficient to cause salivary cortisol concentration to decrease within 15 minutes after the composition is applied when compared with the salivary cortisol concentration measured prior to application.

2. The method of claim 1 wherein the composition is applied prior to retiring.

3. The method of claim 1 wherein the composition is a facial cream, body cream, body oil, bath oil, or fragrance.

4. The method of claim 1 wherein the composition is in the form of a lotion.

5. The method of claim 1 wherein the composition is in the form of an emulsion or gel.

6. The method of claim 1 wherein the composition is in the form of a bath oil.

7. The method of claim 1 wherein the composition is in the form of a facial or body cream.

8. The method of claim 1 wherein the composition is in the form of a body balm.

9. The method of claim 1 wherein the composition is in the form of a spray.

10. A method for inducing a relaxation state comprising topically applying a composition comprising from 0.01 to 60% by weight of the total composition of a Mixture containing 1-45% mandarin oil, 1-45% lavender oil, 1-45% chamomile oil, and 1-45% sweet almond oil with all percentages in the Mixture by weight of the total Mixture.

* * * * *